(12) United States Patent
Yamazaki et al.

(10) Patent No.: US 9,709,749 B2
(45) Date of Patent: Jul. 18, 2017

(54) OPTICAL IMAGING PROBE (71) Applicant: NAMIKI SEIMITSU HOUSEKI KABUSHIKI KAISHA, Tokyo (JP)

(72) Inventors: Hiroshi Yamazaki, Kuroishi (JP); Eri Fukushima, Kuroishi (JP); Takafumi Asada, Kuroishi (JP)

(73) Assignee: Namiki Seimitsu Houseki Kabushiki Kaisha, Tokyo (JP)

(*) Notice: Subject to any disclaimer, the term of this patent is extended or adjusted under 35 U.S.C. 154(b) by 0 days.

(21) Appl. No.: 14/796,504

(22) Filed: Jul. 10, 2015

(65) Prior Publication Data
US 2015/0338580 A1 Nov. 26, 2015

Related U.S. Application Data (63) Continuation of application No. PCT/JP2013/072363, filed on Aug. 22, 2013.

(30) Foreign Application Priority Data

Jan. 25, 2013 (JP) ................................. 2013-012707

(51) Int. Cl.
*G02B 6/36* (2006.01)
*F16C 32/06* (2006.01)
(Continued)

(52) U.S. Cl.
CPC ........ G02B 6/3604 (2013.01); A61B 1/00172 (2013.01); F16C 32/0633 (2013.01); G02B 23/26 (2013.01)

(58) Field of Classification Search
CPC G02B 23/24; G02B 23/2407; G02B 23/2423; G02B 23/2476; G02B 23/26;
(Continued)

(56) References Cited

U.S. PATENT DOCUMENTS 6,023,114 A * 2/2000 Mori ..................... F16C 33/104
310/44
8,055,107 B2 * 11/2011 Masuda ............... A61B 5/0066
385/26
(Continued)

FOREIGN PATENT DOCUMENTS

| JP | 2002-005822 A | 1/2002 |
| JP | 2012-200358 A | 10/2012 |
| WO | 2008/093689 A1 | 8/2008 |

OTHER PUBLICATIONS

International Search Report, PCT/JP2013/072363, Sep. 24, 2013.
(Continued)

*Primary Examiner* — John M Bedtelyon
(74) *Attorney, Agent, or Firm* — Studebaker & Brackett Pc (57) ABSTRACT

Provided is optical imaging probe that is able to obtain stable observation image by optical path correction. It includes a rotation driving source adapted to drive and rotate a rotor; a first single-mode optical fiber inserted and fixed over the axial direction in the rotation center side of the rotor, the front end of which light is able to enter; a second single-mode optical fiber supported at the rear end side of the first single-mode optical fiber in a non-rotatable manner; and a gap and optical path correcting means interposed between the first single-mode optical fiber and the second single-mode optical fiber, and the optical path correcting means is adapted to expand and collimate the light transmitted from one single-mode optical fiber and pass it through the gap, and then guide it to the other single-mode optical fiber.

14 Claims, 7 Drawing Sheets (51) Int. Cl.
*G02B 23/26* (2006.01)
*A61B 1/00* (2006.01)

(58) Field of Classification Search
CPC ............. F16C 32/0633; A61B 1/00013; A61B 1/00096; A61B 1/00098; A61B 1/00117; A61B 1/00163; A61B 1/00165; A61B 1/00167; A61B 1/0017; A61B 1/00172; A61B 1/00177; A61B 1/07
See application file for complete search history.

(56) References Cited

U.S. PATENT DOCUMENTS

| 2010/0105980 A1 | 4/2010 | Shimizu et al. |
| 2012/0245459 A1 | 9/2012 | Senoo |
| 2012/0330101 A1* | 12/2012 | Brennan ............ A61B 1/00096 600/177 |

OTHER PUBLICATIONS

An Office Action issued by the Chinese Patent Office on Jun. 27, 2016, which corresponds to Chinese Patent Application No. 201380071313.X and is related to U.S. Appl. No. 14/796,504; with English language translation.

* cited by examiner

OPTICAL IMAGING PROBE

TECHNICAL FIELD

The present invention relates to an optical imaging probe for taking and observing a light reflected by the object.

BACKGROUND ART

The image diagnosis techniques (optical imaging techniques) have been widely utilized in various sites such as device machine, semiconductor, medical treatment, and so on. For example, the X ray CT, the nuclear magnetic resonance, the ultrasonic observation, and the like are exemplified that are able to take the tomographic image in addition to the general microscopy in the manufacturing site for precision machine, semiconductor, and the like and the medical site.

In recent years, the OCT (Optical Coherent Tomography) technique that utilizes optical coherence has been paid attention as an approach of the image diagnosis. The near infrared ray with the wavelength of 1300 nm is often used for the light source, and the near infrared ray is noninvasive to the organism and is superior in the spatial resolution because of its shorter wavelength than the ultrasonic wave, which allows for the identification of approximately 10 to 20 μm and therefore, in particular, the further use in the medical site is expected. The exemplary structure of the OCT endoscope is as disclosed in Patent document 1, for example.

By the way, in the OCT endoscope disclosed in Patent document 1, the rotational force of a motor is transferred to a rotation shaft via a belt and further transferred to a lens unit via a flexible shaft extending through in an optical sheath. Therefore, ablation powder is likely to occur due to the friction between the inner circumference surface of the optical sheath and the flexible shaft, and rotation unevenness, rotation transfer delay, torque loss, and the like are likely to occur due to the friction, deflection, and/or torsion of the flexible shaft, elastic deformation of the belt, and so on.

Further, as a technique for overcoming the above-described problems, in the invention of Patent document 2, a motor is arranged so as to face the front end of an optical fiber and a reflection mirror is provided at the front end surface of the rotation shaft of the motor. In this invention, however, the body of the motor is located more front than the reflection mirror, which may cause the problems that the power supply cable for the motor may be bent toward the optical fiber side, that the power supply cable may be located in the side of the reflection mirror and block the light reflected by the reflection mirror and thus a part of the whole 360-degree circumference may be a shade resulting in the limitation of the angle of view, and that a protruding part that is more front than the reflection mirror (a part incorporating the motor body) may come into contact with the object resulting in the limitation of the imaging range in the probe axis direction. Further, when the motor is rotated continuously at a high speed, the deviation of the film pressure of the lubricating oil at the bearing part is likely to cause rotation unevenness, axis vibration, and the like called as jitter (the phenomenon in which the rotation angle fluctuates), face tangle error (the phenomenon in which the rotation end surface tilts), and whirl (the phenomenon in which the rotation axis vibrates).

Furthermore, the axis displacement and the like due to them may cause the light transmission loss to be increased.

RELATED ART DOCUMENT

Patent Literatures

[Patent Document 1] Japanese Patent No. 3885114
[Patent Document 2] Japanese Patent No. 4461216

DISCLOSURE OF THE INVENTION

Problems to be Solved by the Invention

The present invention has been achieved taking into consideration of the above-described conventional circumstances, and its objects are to provide an optical imaging probe that is able to obtain a stable observation image by reducing the occurrence of the rotation transfer delay, the torque loss, and the light transmission loss, preventing the rotation unevenness, the axis vibration, the friction, and the rotation transfer delay of the rotation part and the limitation of the angle of view that a part of the whole 360-degree circumference is shaded, and preventing the limitation of the imaging range in the probe circumference direction and the axial direction.

Solutions to the Problems

One of the solutions to overcome the above problems is an optical imaging probe for guiding rearward a light entering the front end that includes a rotation driving source adapted to drive and rotate a rotor; a first single-mode optical fiber inserted and fixed over the axial direction in the rotation center side of the rotor, the front end of which a light is able to enter; a second single-mode optical fiber supported at the rear end side of the first single-mode optical fiber in a non-rotatable manner; and a gap and optical path correcting means interposed between the first single-mode optical fiber and the second single-mode optical fiber, and the optical path correcting means is adapted to expand and collimate a light transmitted from one of the single-mode optical fibers and pass it through the gap, and then guide it to the other single-mode optical fiber.

Advantage of the Invention

The present invention is configured as described above, so that a stable observation image can be obtained compared to the conventional art.

DESCRIPTION OF EMBODIMENTS

The first feature of the present embodiment includes, in an optical imaging probe for guiding rearward a light entering the front end: a rotation driving source adapted to drive and rotate a rotor; a first single-mode optical fiber inserted and fixed over the axial direction in the rotation center side of the rotor, the front end of which a light is able to enter; a second single-mode optical fiber supported at the rear end side of the first single-mode optical fiber in a non-rotatable manner; and a gap and optical path correcting means interposed between the first single-mode optical fiber and the second single-mode optical fiber, and the optical path correcting means is adapted to expand and collimate the light transmitted from one of the single-mode optical fibers and pass it through the gap, and then guide it to the other single-mode optical fiber (see FIGS. 1 to 6).

According to this configuration, the light emitted from one of the single-mode optical fibers is expanded and collimated to be guided to the other single-mode optical fiber, so that the light transmission loss can be reduced between the single-mode optical fibers even when a displacement may occur between the centers of one single-mode optical fiber and the other single-mode optical fiber.

The second feature is that, in addition to the first feature, the optical path correcting means includes first optical path correcting means connected to the first single-mode optical fiber and second optical path correcting means connected to the second single-mode optical fiber, and has the gap between the two optical path correcting means (see FIGS. 1 to 4).

According to this configuration, the light passing through the gap between the one optical path correcting means and the other optical path correcting means is expanded and collimated to make a relatively thick light, so that the light transmission loss can be reduced even when a displacement may occur between the centers of one single-mode optical fiber and the other single-mode optical fiber.

The third feature is that, in addition to the second feature, it further includes a tubular rotation shaft fixed over the axial direction in the rotation center side of the rotor and supported protruding its end side from the rotor in the axial direction in a rotatable manner, and a connection portion of the first single-mode optical fiber and the first optical path correcting means is disposed inside the tubular rotation shaft (FIGS. 1 to 4).

This configuration allows for the reduction of the axis displacement at the connection portion of the first single-mode optical fiber and the first optical path correcting means and further allows for the reinforcement of the connection portion by the tubular rotation shaft.

Figure 3:
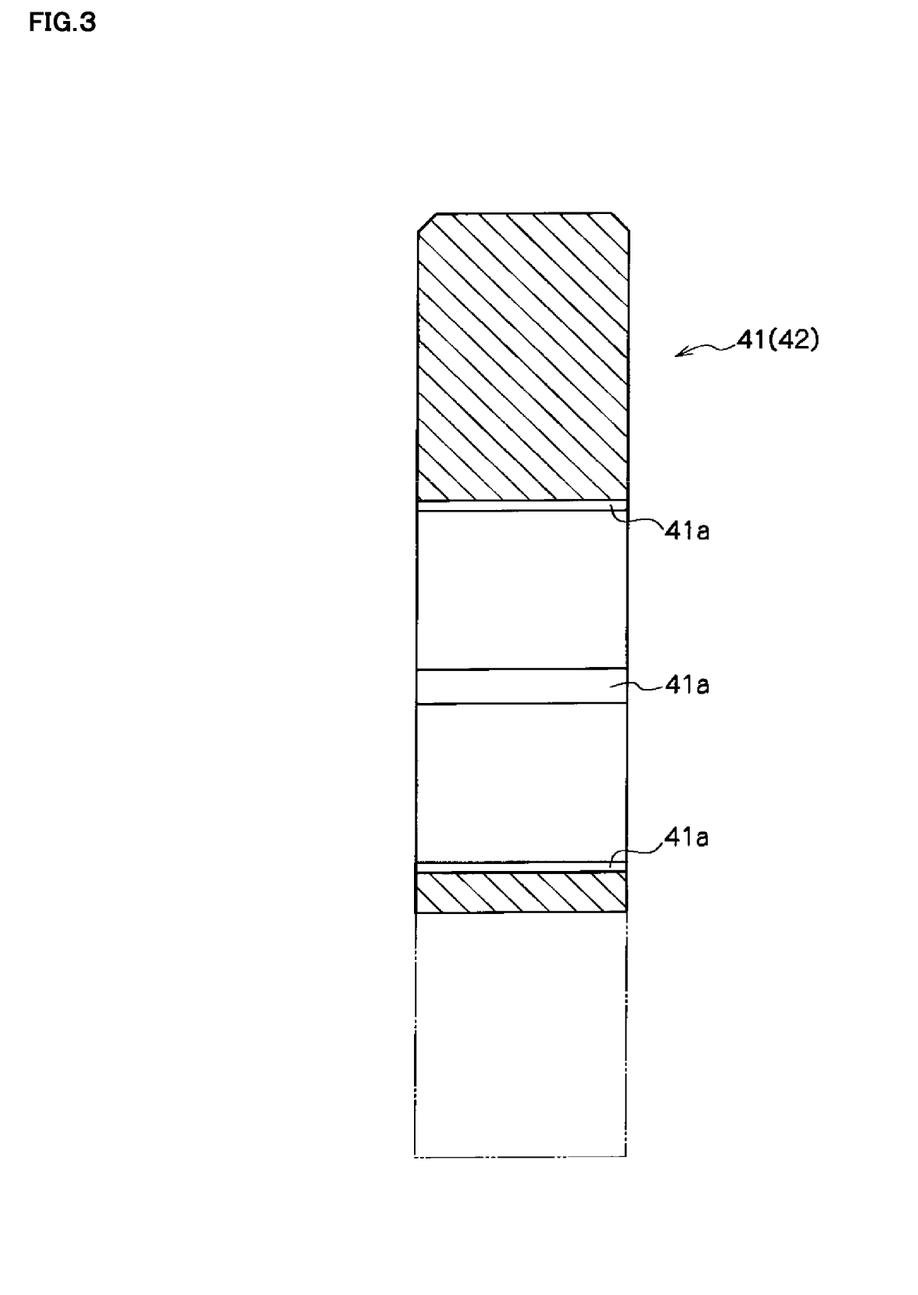
FIG. 3 is an enlarged cross-sectional view illustrating an example of a bearing member.

The fourth feature is that, in addition to the third feature, it further includes a bearing member for supporting the tubular rotation shaft in a rotatable manner, and the bearing member includes a dynamic pressure bearing adapted to generate a high lubricating oil film pressure locally at multiple positions in the circumference direction (see FIG. 3).

According to this configuration, the bearing member forms the dynamic pressure bearing that generates a high lubricating film oil pressure locally at the multiple positions in the circumference direction, so that the lubricating oil film pressure can be distributed in the circumference direction allowing for the reduction in the rotation unevenness, the axis vibration, and the like of the rotation part. Therefore, the light transmission loss between the single-mode optical fibers can be further reduced.

Figure 1:
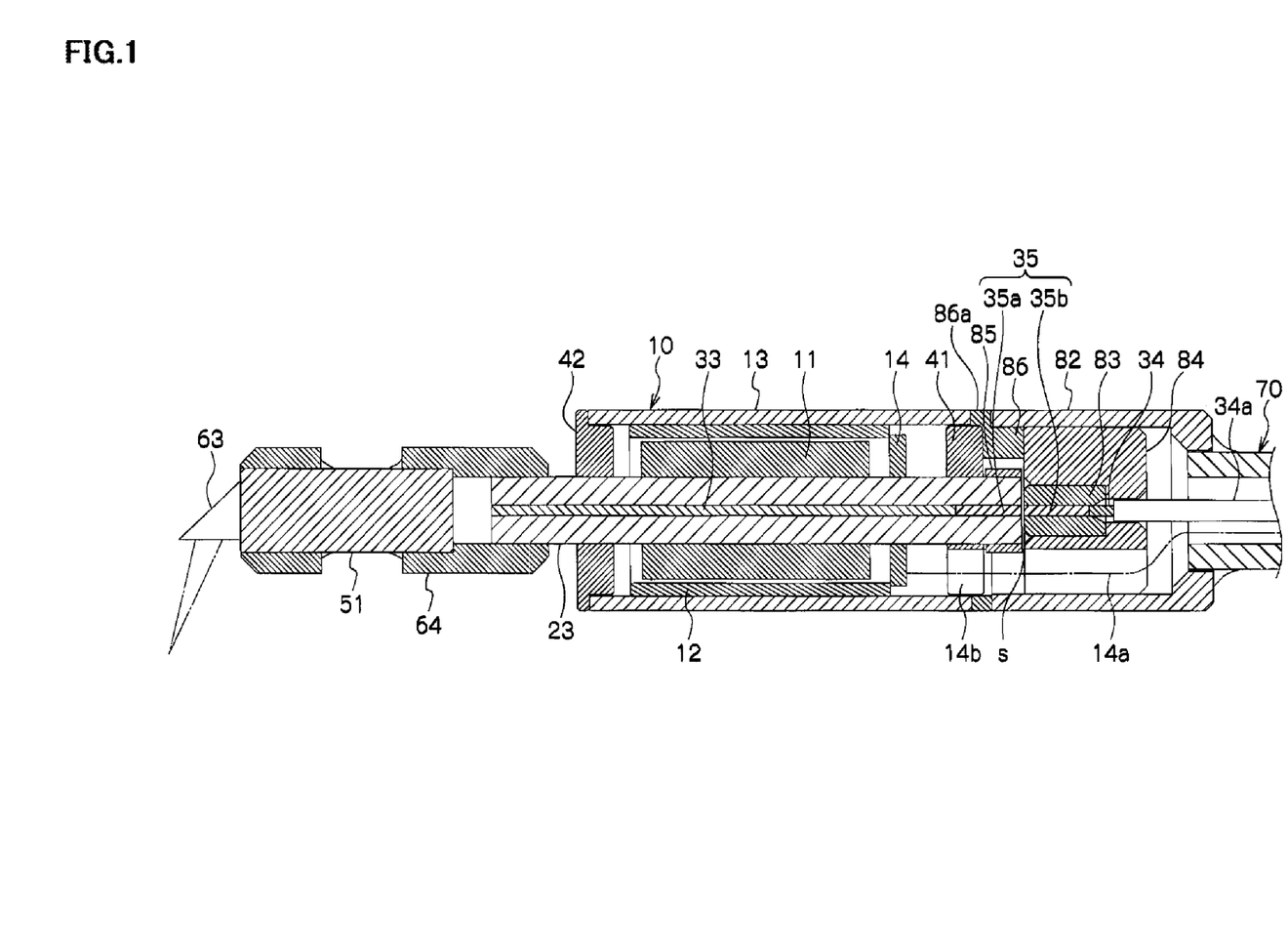
FIG. 1 is a cross-sectional view illustrating an example of an optical imaging probe according to the present invention.
Figure 2:
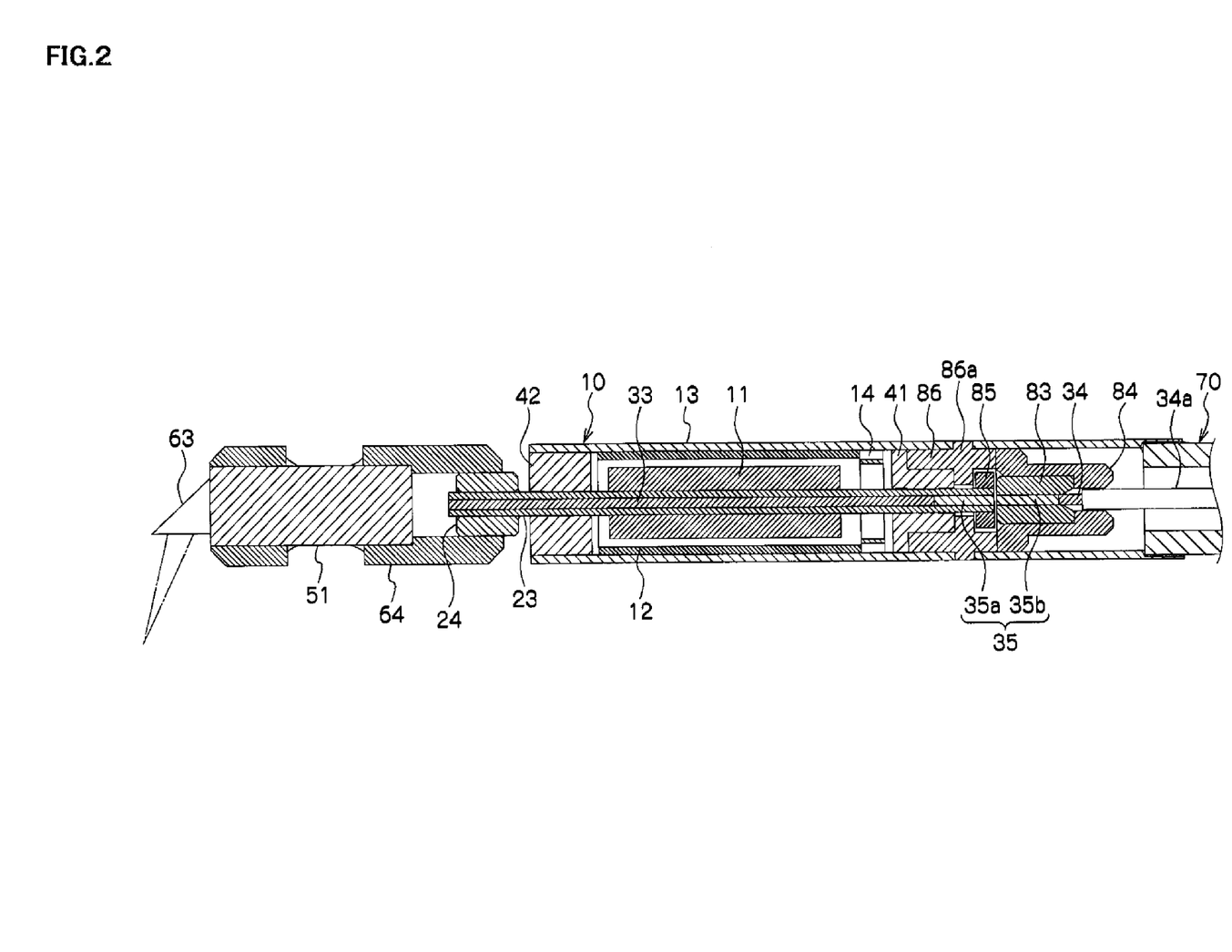
FIG. 2 is a cross-sectional view illustrating another example of an optical imaging probe according to the present invention.

The fifth feature is that, in addition to any one of the first to fourth features, an optical path conversion element adapted to convert the direction of the light guided by the single-mode optical fiber into the intersecting direction with respect to the axial direction of the tubular rotation shaft is provided in the front side of the first single-mode optical fiber (see FIGS. 1 and 2).

This configuration allows the stable observing image to be obtained in the range of the angle of 360 degrees in the probe outer circumference.

The sixth feature is that, in addition to any one of the first to fifth features, the rotor is rotated continuously at the number of revolution of 400 rpm or more and 3600 rpm or less.

According to this configuration, even when the displacement between the centers of one single-mode optical fiber and the other single-mode optical fiber may occur due to the rotation unevenness, the axis vibration, and the like that could occur when the rotor is continuously rotated at a high speed, the light transmission loss can be effectively reduced by the optical path correcting means interposed between them.

Further, other feature is that a plurality of the bearing members are provided to support both sides in the axial direction of the tubular rotation shaft, and at least the bearing member which is located nearest the gap among these plurality of bearing members configures the dynamic pressure bearing.

This configuration allows the dynamic pressure bearing located near the gap to reduce the axis displacement of the other single-mode optical fiber with respect to one single-mode optical fiber.

Further, other feature is that light converging means adapted to converge the light emitted forward from the first single-mode optical fiber is provided between the optical path conversion element and the front end of the first single-mode optical fiber (see FIGS. 1 to 3).

This configuration allows the light emitted forward from the first single-mode optical fiber at the front end to converge to effectively irradiate the object.

Next, the preferred examples of the present embodiment having the above features will be described in detail based on the drawings.

EXAMPLE 1

FIG. 1 illustrates an example 1 of the optical imaging probe according to the present invention.

The optical imaging probe includes: a rotation driving source 10 adapted to drive and rotate a rotor 11; a tubular rotation shaft 23 inserted and fixed over the axial direction in the rotation center side of the rotor 11; a first single-mode optical fiber 33 inserted in the tubular rotation shaft 23, the front end of which a light is able to enter; a second single-mode optical fiber 34 supported in the rear side of the first single-mode optical fiber 33 in a non-rotatable manner; a gap s and optical path correcting means 35c interposed between the first single-mode optical fiber 33 and the second single-mode optical fiber 34 (see FIG. 5); bearing members 41 and 42 supporting the tubular rotation shaft 23 in a rotatable manner; light converging means 51 adapted to converge the light emitted forward from the first single-mode optical fiber 33; and an optical path conversion element 63 adapted to convert the direction of the light guided by the first single-mode optical fiber into the intersecting direction with respect to the axial direction of the tubular rotation shaft 23.

The rotation driving source 10 is an electric motor of the inner rotor type (see FIG. 1) including the rotatable rotor 11, an electromagnetic coil 12 covering the peripheral of the rotor 11, a cylindrical front housing 13 (stator) covering the peripheral of the electromagnetic coil 12, a substrate 14 adapted to supply electric power to the electromagnetic coil 12, and so on, and is controlled so as to continuously rotate at a predetermined number of revolutions.

The rotor 11 is arranged in a cylindrical shape having a permanent magnet, and continuously rotated by the electromagnetic effect in relation with the electromagnetic coil 12.

The electromagnetic coil 12 is provided in substantially a cylindrical manner with a predetermined clearance to the outer circumference surface of the rotor 11, and fixed to the inner circumference surface of the front housing 13 (stator) in an non-rotatable manner.

The substrate 14 is fixed to the rear end surface of the electromagnetic coil 12 in substantially an angular manner, and supplies, to the electromagnetic coil 12, the control current supplied from the power supply cable 14a.

The power supply cable 14a is guided rearward through a notched through part 14b formed in a bearing member 41, a connection member 86 and a holder 84 described later, and is further connected to the control circuit in the OCT apparatus through inside the long cylindrical sheath 70. It is noted that the through part 14b may be a through hole.

The front housing 13 (stator) is formed in a cylindrical shape from a magnetic material (for example, permalloy and the like), and works to enhance the electromagnetic force generated by the electromagnetic coil 12.

The bearing members 41 and 42 are supported by the front end side and the rear end side of the front housing 13. Further, a cylindrical rear housing 82 with substantially the same diameter as the front housing 13 is connected to the rear end side of the front housing 13 and the bearing member 41 via the connection member 86, and the sheath 70 is connected to the rearmost end of the rear housing 82.

The connection member 86 connects the front housing 13 and the rear end of the bearing member 41 to the rear housing 82. The connection member 86 is substantially the column member in which the tubular rotation shaft 23 is inserted in the shaft center side in a rotatable manner and the power supply cable 14a is inserted in the notch in the outer circumference side, and is fixed in non-rotatable manner by having an edge 86a protruding outward in the radial direction from the outer circumference surface held between the cylindrical front housing 13 and the rear housing 82 and fitting itself into the inner circumference surface of the rear housing 82.

The rear housing 82 is substantially a cylindrical member fitted into the outer circumference surface of the connection member 86 and, in its rear end side, communicates into the long cylindrical sheath 70.

Further, the tubular rotation shaft 23 is a long cylindrical member made of a hard material such as metal and is inserted and fixed on the rotation center side of the rotor 11, and its front end and rear end sections protrude out of the end surfaces of the axial direction of the rotor 11.

The rear end side of tubular rotation shaft 23 is supported by the bearing member 41 in its rear side in a rotatable manner, and the front end side of the tubular rotation shaft 23 is supported by the bearing member 42 in its front side in a rotatable manner and protrudes forward than the bearing member 42.

Further, within the tubular rotation shaft 23, the first single-mode optical fiber 33 is inserted and fixed in the front side and first optical path correcting means 35a is inserted and fixed in the rear side.

The bearing members 41 and 42 configure the dynamic bearings adapted to generate a high film pressure of the lubricating oil locally at multiple positions in the circumference direction.

Each of the bearing members 41 and 42 is formed in substantially a cylindrical shape by a hard material with a good abrasion resistance property such as bronze, sintered metal, and the like and, in its inner circumference side, the tubular rotation shaft 23 is inserted and supported in a rotatable manner interposing the lubricating oil.

In the inner circumference surface of each of the bearing members 41 and 42, as illustrated in FIG. 3, a plurality of grooves 41a extending in the axial direction are formed by a predetermined pitch in the circumference direction. Each groove 41a continues from one end to the other end of the bearing members 41 and 42 in the axial direction.

A plurality of grooves 41a work so as to distribute, in the circumference direction, the pressure of the lubricating oil film (referred to as lubricating oil film pressure) inserted between each of the bearing members 41 and 42 and the tubular rotation shaft 23.

Figure 8:
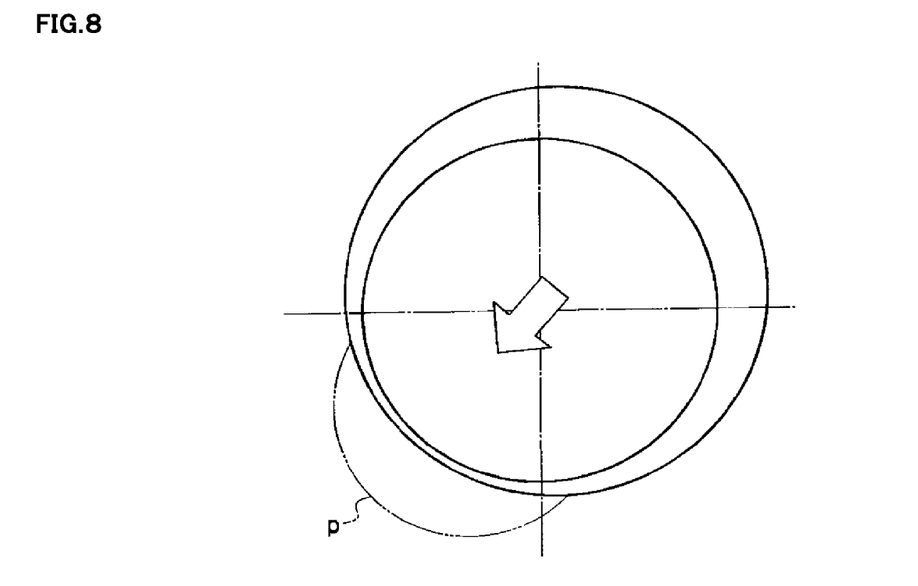
FIG. 8 is a schematic view illustrating a distribution of lubricating oil film pressure in the case of the complete-circle bearing member.

That is, if a complete-circle bearing member without the groove 41a were used, the lubricating oil film pressure p would be offset and locally increased at a part of the inner circumference surface of the bearing member in the circumference direction as illustrated in FIG. 8, which is likely to cause rotation unevenness, axis vibration, and the like called as jitter (the phenomenon in which the rotation angle fluctuates), face tangle error (the phenomenon in which the rotation end surface tilts), and whirl (the phenomenon in which the rotation axis vibrates).

Figure 7:
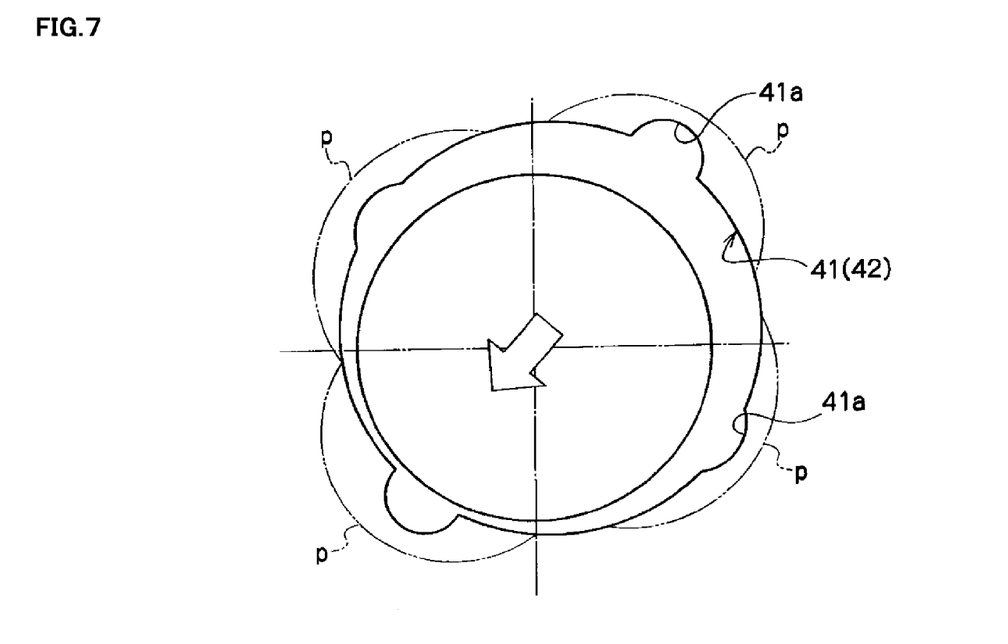
FIG. 7 is a schematic view illustrating a distribution of the lubricating oil film pressure in the bearing structure of the present embodiment.

According to the bearing members 41 and 42 of the present embodiment, however, the lubricating oil film pressure p is distributed in the multiple positions corresponding to the grooves 41a in the circumference direction and is higher near each groove 41a as illustrated in FIG. 7. This allows for the significant reduction of the jitter, the face tangle error, the whirl, and the like.

It is noted that, while FIG. 7 schematically illustrates the bearing structure according to the present invention and the grooves 41a, 41a neighboring in the circumference direction are different in depth, the depth of a plurality of grooves 41a is set to be the same in a preferred example of the present embodiment. The depth, the width, and the number of these grooves 41a are properly set so as to effectively reduce the occurrence of the jitter, the face tangle error, the whirl, and the like. While the bearing member 41 as depicted as an example has four grooves 41a by the same pitch, other preferred example has eight by the same pitch.

According to an example of the present embodiment, the inner diameter of the bearing or the outer diameter is approximately 0.3 mm to 1.0 mm, the gap in the radial direction is designed to the range from 1 micrometer to 3 micrometers.

Further, according to an example of the present embodiment, while the groove 41a is provided in parallel with respect to the shaft (that is, at an angle of 90 degrees with respect to the direction in which the lubricating fluid rotates and flows) in order to provide the same performance in any case where the rotation direction of the shaft is forward or reverse, any proper angle may be provided with respect to the shaft when the rotation direction is defined in one direction, and the both allow for the preferable performance.

Further, according to the experimental result by the inventors of the present application, it has been confirmed that the design that the number of the grooves 41a ranges four to sixteen and its depth ranges 1 micrometer to a few micrometers allows for the preferable performance, but, when out of these ranges, it is likely to degenerate the optical performance due to the rotation vibration or the vibrating rotation.

The rear bearing member 41 is fitted into the inner circumference surface of the front housing 13, has the tubular rotation shaft 23 inserted in the shaft center side and supports it in a rotatable manner, and fits the connection member 86 into the rear outer circumference surface.

Further, the front bearing member 42 is fitted into the inner circumference surface of the front end side of the front housing 13 and has the tubular rotation shaft 23 inserted in the shaft center side and supports it in a rotatable manner.

The first single-mode optical fiber 33 is formed with a core in the center side and a clad covering its outer peripheral. The first single-mode optical fiber 33 is formed slightly shorter than the tubular rotation shaft 23 and inserted near the front side within the tubular rotation shaft 23 with its end forming substantially a flat plane with the front end of the tubular rotation shaft 23. The first single-mode optical fiber 33 contacts, by its outer surface, with the inner surface of the tubular rotation shaft 23 over substantially the whole length in the axial direction and substantially the whole circumference, and rotates with the tubular rotation shaft 23 in an integral manner.

The second single-mode optical fiber 34 is disposed in the rear side of the first single-mode optical fiber 33 in a coaxial manner interposing the optical path correcting means 35 and the gap s, and supported in a non-rotatable manner.

Similarly to the first single-mode optical fiber 33, the second single-mode optical fiber 34 is formed with a core in the center side and a clad covering its outer peripheral, and its rear side other than a part of the front end side is covered with a protection coating 34a. The rear side of the second single-mode optical fiber 34 is inserted in the sheath 70 and connected to the OCT apparatus.

The optical path correcting means 35 is configured to expand and collimate the light transmitted from one single-mode optical fiber 33 (or 34) to pass it in the gap s and then converge and guide it to the other single-mode optical fiber 34 (or 33).

Figure 4:
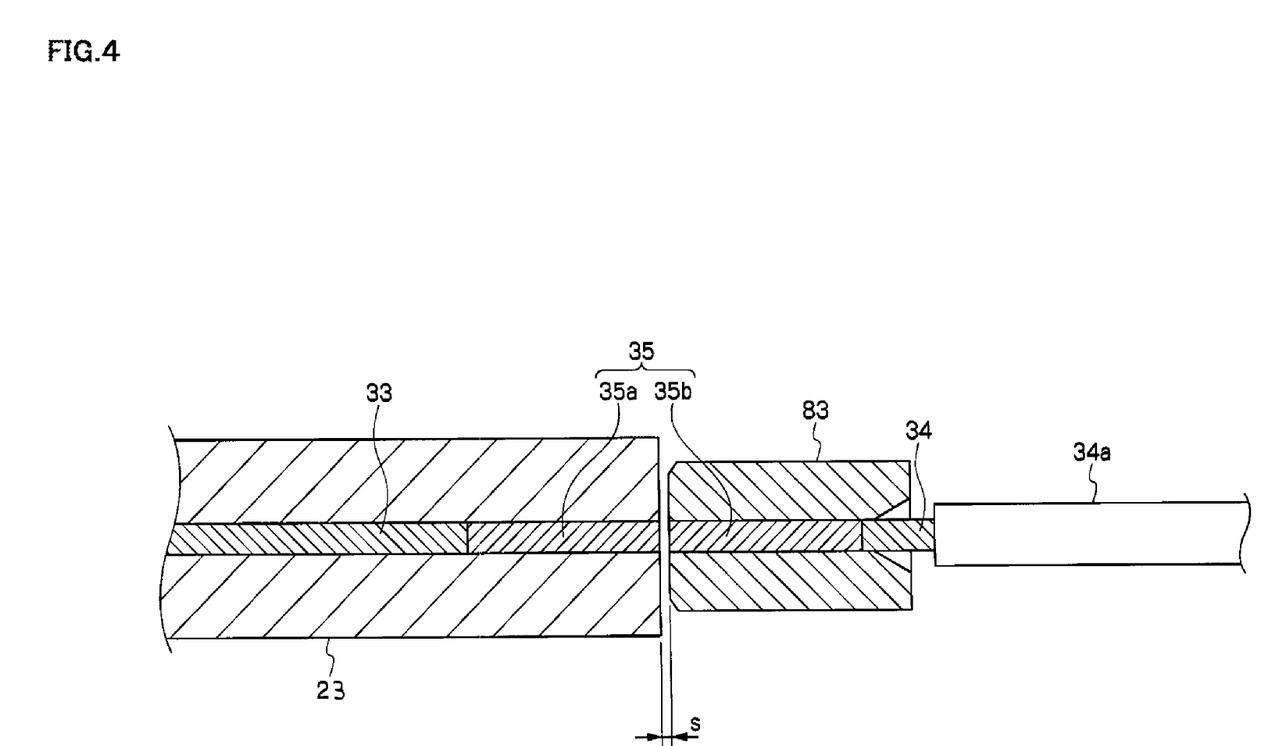
FIG. 4 is an enlarged cross-sectional view illustrating an example of a connection between two single-mode optical fibers.

With respect to the example illustrated in FIG. 4, in details, the optical path correcting means 35 includes first optical path correcting means 35a connected to the first single-mode optical fiber 33 and second optical path correcting means 35b connected to the second single-mode optical fiber 34 and has the gap s between these two optical path correcting means 35a and 35b.

The first optical path correcting means 35a is a graded index optical fiber adapted to expand and collimate the light guided rearward from the first single-mode optical fiber 33.

The first optical path correcting means 35a is inserted in the rear end side of the tubular rotation shaft 23 such that its rear end forms substantially a flat plane with the rear end of the tubular rotation shaft 23, and is connected to the rear end of the first single-mode optical fiber 33 in a coaxial manner inside the tubular rotation shaft 23.

While the first optical path correcting means 35a may be connected to the first single-mode optical fiber 33 by a welding, the first optical path correcting means 35a and the first single-mode optical fiber 33 may be arranged by a pressure welding in the axial direction as another example.

Also, the second optical path correcting means 35b is a graded index optical fiber adapted to expand and collimate the light irradiated forward from the second single-mode optical fiber 34.

While the second optical path correcting means 35b may be connected to the second single-mode optical fiber 34 by a welding, the second optical path correcting means 35b and the second single-mode optical fiber 34 may be arranged by a pressure welding in the axial direction as another example.

The graded index optical fibers used as the first and second optical path correcting means 35a and 35b are formed in a proper length so as to expand the light irradiated from the first or second single-mode optical fiber 33 or 34 to make substantially the parallel and relatively wide light and, for example, formed in a length corresponding to one-fourth of the meandering range of the light traveling within the core or an odd multiple thereof.

It is noted that another example of the first and second optical path correcting means 35a and 35b may be the GRIN lens (refractive index distribution lens), other lens, and the like.

The second optical path correcting means 35b is fixed to the inner circumference surface of the rear housing 82 in a non-rotatable manner via a cylindrical holding member 83 and a holder 84 (see FIG. 1).

The cylindrical holding member 83 is a cylindrical member covering the second optical path correcting means 35b over the whole length and inserting the front end of the second single-mode optical fiber 34 therein.

The inner circumference surface of the cylindrical holding member 83 contacts with the outer circumference surface of the second optical path correcting means 35b and holds the second optical path correcting means 35b in a non-rotatable manner (see FIG. 1).

The holder 84 is a cylindrical member having a notch in a part of the outer circumference through which the power supply cable 14a passes, and inserts and fixes the cylindrical holding member 83 at its front side of the center and inserts and fixes the protection coating 34a of the second single-mode optical fiber 34 at its rear side (see FIG. 1).

As described above, since the gap s is secured between the first optical path correcting means 35a and the second optical path correcting means 35b, the first optical path correcting means 35a is able to freely rotate.

The width of the gap s is properly set so that the light transmission can be effectively made between the first optical path correcting means 35a and the second optical path correcting means 35b.

In addition, in FIG. 1, the reference sign 85 represents a positioning member fixed on the outer circumference surface of the rear side of the tubular rotation shaft 23. The positioning member 85 is located between the rear bearing member 41 and the holder 84, restricts the forward movement of the tubular rotation shaft 23 by the contact with the bearing member 41, and restricts the rearward movement of the tubular rotation shaft 23 by the contact with the holder 84.

Then, the light converging means 51 is fixed to the part protruding forward from the front bearing member 41 in the tubular rotation shaft 23 in a coaxial manner via a support bracket 64, and the optical path conversion element 63 is further fixed to the front end of the light converging means 51 in a coaxial manner (see FIG. 1).

The support bracket 64 is a cylindrical member connected to the front end of the tubular rotation shaft 23 in substantially a coaxial manner, and inserts and fixes the front end of the tubular rotation shaft 23 in its rear end side and inserts and fixes the rear end of the light converging means 51 described later in its front end side.

The light converging means 51 is located between the optical path conversion element 63 and the front end of the first single-mode optical fiber 33 and disposed in front of the first single-mode optical fiber 33 with a gap (see FIG. 1), and converges the light emitted forward from the first single-mode optical fiber 33.

While the light converging means 51 is substantially the column-shaped GRIN lens (the refractive index distribution lens) according to the depicted example, it may be replaced with a proper length of graded index optical fiber, a lens with other shape than the column, and the like as another example.

The optical path conversion element 63 is a prism adapted to convert the direction of the light emitted forward with being guided by the first single-mode optical fiber 33 and converged by the light converging means 51 into the intersecting direction with respect to the axial direction of the first single-mode optical fiber 33. According to the depicted example, the light emitted from the optical path conversion element 63 is guided in the direction slightly inclined forward from the orthogonal direction (see the two-dot chain line of FIG. 1).

Next, with respect to the optical imaging probe of FIG. 1 described above, its distinctive effects and advantages will be described in detail.

First, in response that electric power is supplied to the rotation driving source 10 by the power supply cable 14a, the rotation driving source 10 rotates the rotor 11, the tubular rotation shaft 23, the first single-mode optical fiber 33, the first optical path correcting means 35a, the support bracket 64, the light converging means 51, the optical path conversion element 63, and so on continuously at a high speed. The revolving speed at this time is adjustable within the range of 0 to 3600 rpm, preferably set to 400 rpm or more and 3600 rpm or less so that the tubular rotation shaft 23 float in the lubricating oil at the bearing part, and set to approximately 1800 rpm according to the particularly preferable embodiment.

Then, in response that a light (in detail, the near infrared ray) is supplied to the starting end of the second single-mode optical fiber 34 from the OCT apparatus, the light passes in the second single-mode optical fiber 34 and is transmitted from the front end of the second single-mode optical fiber 34 to the second optical path correcting means 35b, transmitted from the second optical path correcting means 35b to the first optical path correcting means 35a via the gap s, and then transmitted from the first optical path correcting means 35a to the first single-mode optical fiber 33.

In details of this light transmission, the light transmitted from the second single-mode optical fiber 34 to the second optical path correcting means 35b is expanded and collimated within the second optical path correcting means 35b, and thereby becomes relatively thick and substantially a parallel beam and passes through the gap s, and enters the rear end of the first optical path correcting means 35a. The incident light is then converged inside the first optical path correcting means 35a and transmitted to the first single-mode optical fiber 33.

Then, the light travels forward inside the first single-mode optical fiber 33 is emitted forward from the front end of the first single-mode optical fiber 33, enters the light converging means 51, converges inside the light converging means 51 to propagate to the optical path conversion element 63, and is direction-converted to the intersecting direction by the optical path conversion element 63 and irradiated to the object.

Further, the light reflected by the object passes the path opposite to the above, first enters the optical path conversion element 63 to be direction-converted and is transmitted rearward by the light converging means 51, the first single-mode optical fiber 33, the first optical path correcting means 35a, the second optical path correcting means 35b, and the second single-mode optical fiber 34 back to the OCT apparatus. The OCT apparatus analyses the returned reflection light and images the range of 360-degree peripheral of the front end side of the optical imaging probe in real time.

As described above, in rotating the optical path conversion element 63 and the like, the rotational force of the rotor 11 is transferred to the optical path conversion element 63 via the tubular rotation shaft 23 that is a rigid body without being transferred via the conventional flexible shaft, so that the occurrence of the rotation transfer delay, the torque loss, and the like can be reduced. Moreover, the bearing members 41 and 42 form the dynamic pressure bearings that generates a high lubricating film oil pressure locally at the multiple positions in the circumference direction, so that the lubricating oil film pressure can be distributed in the circumference direction allowing for the reduction in the rotation unevenness, the axis vibration, and the like of the rotation part.

Furthermore, even when a slight axis vibration occurs, since the light is expanded and collimated between the first optical path correcting means 35a and the second optical path correcting means 35b, the light transmission loss can be reduced.

Therefore, as a result of the above, a stable observation image can be obtained.

Further, employed is the structure that the main components such as the rotation driving source and the like are not disposed more front than the optical path conversion element 63, which allows for the simple arrangement of the power supply cable 14a and thus can prevent the limitation of the imaging range in the probe circumference direction and the forward movement by the power supply cable 14a.

EXAMPLE 2

Next, described will be an example 2 of the optical imaging probe according to the present invention (see FIG. 2).

In the optical imaging probe illustrated in FIG. 2, the outer diameter of the rotation driving source 10 is reduced to substantially the same as the outer diameter of the support bracket 64 compared to the optical imaging probe illustrated in FIG. 1 and thus the fundamental structure is the same as that in FIG. 1.

In FIG. 2, the reference sign 24 represents an angular spacer 24 for connecting the tubular rotation shaft 23 formed thinner than that of FIG. 1 to the support bracket 64.

Further, in FIG. 2, although the depiction of the power supply cable is omitted, the power supply cable passes in the position shifted by approximately 90 degrees in the circumference direction and passes within the notch and sheath 70 similarly to FIG. 1 and reaches the OCT apparatus from the substrate 14.

Therefore, according to the optical imaging probe illustrated in FIG. 2, similarly to that in FIG. 1, the rotational force of the rotor 11 is transferred to the optical path conversion element 63 via the tubular rotation shaft 23 that is a rigid body without transferred via the conventional flexible shaft in rotating the optical path conversion element 63 and the like, so that the occurrence of the rotation transfer delay, the torque loss, and the like can be reduced. Moreover, the bearing members 41 and 42 form the dynamic pressure bearings that generates a high lubricating film oil pressure locally at the multiple positions in the circumference direction, so that the lubricating oil film pressure can be distributed in the circumference direction allowing for the reduction in the rotation unevenness, the axis vibration, and the like of the rotation part.

Furthermore, even when a slight axis vibration occurs, since the light is expanded and collimated between the first optical path correcting means 35a and the second optical path correcting means 35b, the light transmission loss can be reduced.

Therefore, as a result of the above, a stable observation image can be obtained.

Further, employed is the structure that the main components such as the rotation driving source and the like are not disposed more front than the optical path conversion element 63, which allows for the simple arrangement of the power supply cable and thus can prevent the limitation of the imaging range in the probe circumference direction and the forward movement by the power supply cable.

Figure 5:
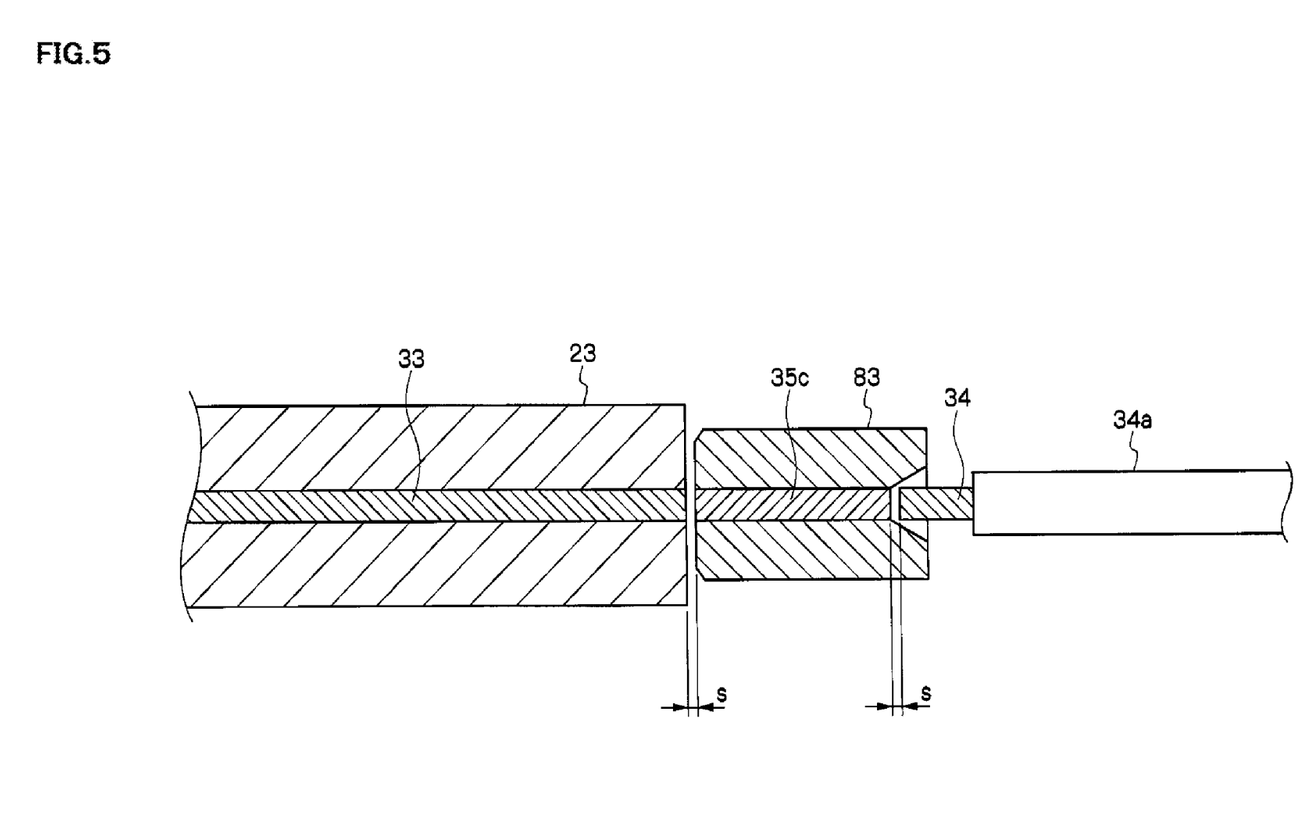
FIG. 5 is an enlarged cross-sectional view illustrating another example of a connection between two single-mode optical fibers.
Figure 6:
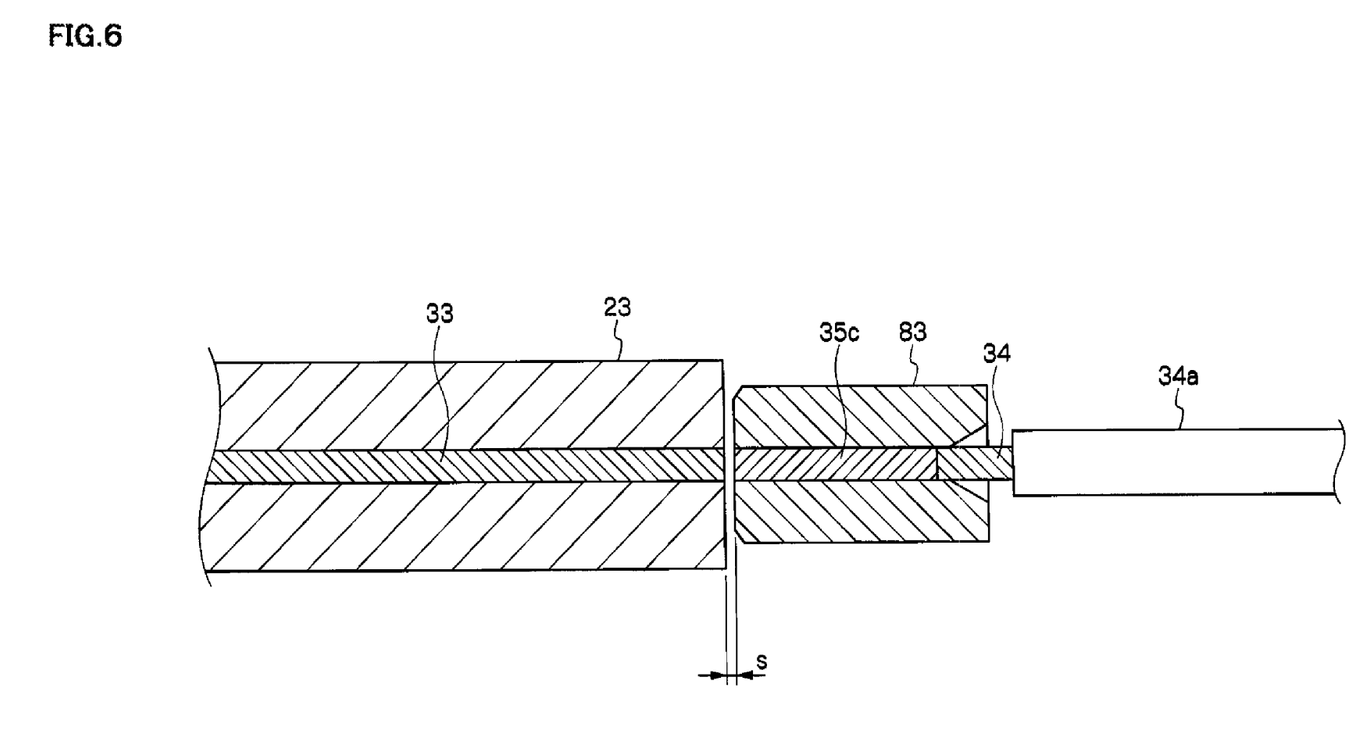
FIG. 6 is an enlarged cross-sectional view illustrating another example of a connection between two single-mode optical fibers.

It is noted that, while the optical imaging probes illustrated in FIG. 1 and FIG. 2 are configured with two optical path correcting means 35a and 35b as a preferable connecting structure of the first single-mode optical fiber 33 and the second single-mode optical fiber 34, it may be configured with a single optical path correcting means 35c as the form illustrated in FIG. 5 and FIG. 6 as other examples.

In details, in the form illustrated in FIG. 5, the single optical path correcting means 35c is disposed between the first single-mode optical fiber 33 and the second single-mode optical fiber 34, and the gaps s are provided between the optical path correcting means 35c and the first single-mode optical fiber 33 and between the optical path correcting means 35c and the second single-mode optical fiber 34, respectively.

Also in the form illustrated in FIG. 6, the single optical path correcting means 35c is disposed between the first single-mode optical fiber 33 and the second single-mode optical fiber 34, the gap s is provided between the optical path correcting means 35c and the first single-mode optical fiber 33, and the optical path correcting means 35c and the second single-mode optical fiber 34 are connected in contact with each other.

In the forms illustrated in FIG. 5 and FIG. 6, the length of the optical path correcting means 35c and the width of the gap s are properly set so that the light emitted from the optical path correcting means 35 is expanded and collimated to reduce the light transmission loss when the axis vibration may occur.

Further, while the dynamic pressure bearing (that may be referred to as the incomplete-circle dynamic pressure bearing or the multi-arc bearing) having a plurality of grooves 41a with intervals in the circumference direction is used as the bearing members 41 and 42 in the optical imaging probes illustrated in FIG. 1 to FIG. 2, the bearing members 41 and 42 may be the dynamic pressure bearings that generate a high lubricating oil film pressure locally at the multiple positions in the circumference direction and, for example, it is possible to use a form having a plurality of grooves in the axis side with a pitch in the circumference direction, a form in which a plurality of arc members divided in the circumference direction are combined in substantially a cylindrical shape (that may be referred to as the segment bearing), and other dynamic pressure bearing. However, the complete-circle bearing is not included as these bearing members 41 and 42.

Further, while both of the front and the rear bearing members 41 and 42 are configured as the dynamic pressure bearing in the optical imaging probes illustrated in FIG. 1 to FIG. 2, either one of them may be configured as the dynamic pressure bearing and the other may be configured as other bearing including the complete-circle bearing, as another example. In this case, it is preferable that the bearing member 41 near the optical path correcting means 35 is the dynamic pressure bearing in terms of reduction of the axis displacement.

Further, while both sides of the tubular rotation shaft 23 are supported by the bearing members 41 and 42 as a preferable form in the optical imaging probes illustrated in FIG. 1 to FIG. 2, one of the sides of the tubular rotation shaft 23 may be supported by one bearing member 41 (or 42) only in a cantilevered beam manner as another example. In this case, it is preferable that the bearing member 41 near the optical path correcting means 35 is supported in terms of reduction of the axis displacement.

Further, while the optical imaging probes illustrated in FIG. 1 to FIG. 2 have the advantages of the reduced axis vibration and optical transmission loss when continuously rotated at a high speed, the optical imaging probe may be used in a low speed rotation or an intermittent rotation as another example.

Further, while the arrangement that the light emitted from the front end of the optical imaging probe is reflected to the object and the reflected light is taken to be transmitted to the OCT apparatus (an interactive communication arrangement) is employed in the optical imaging probes illustrated in FIG. 1 to FIG. 2, employed may be the arrangement that the reflection light from a different light source than the optical imaging probe is taken to be transmitted to the OCT apparatus (an unidirectional communication arrangement).

It is noted that there is an applicable design range in the bearing structure to which the present embodiment can be applied. That is, the smooth rotation with low rotation loss is essential, and the use of unnecessarily high viscosity lubricating fluid or the bearing design with extremely high rigidity will result in the shortage of motor output, which may degenerate the accuracy of the angular velocity of the motor and thus causes increased jitter. Contrarily, in the dynamic pressure bearing, the design with extremely low rigidity will result in the shortage of dynamic pressure even at the number of revolutions of 400 rpm, which may cause much axis vibration and thus degenerate the performance. Further, such bearing with low rigidity is likely to cause increased vibration at the number of revolutions over 3600 rpm due to the centrifugal force generated from the rotation unit (it is increased proportionally to a square of the number of revolutions) resulting in the degeneration of the performance.

The Applicants have confirmed through experiments that the revolutions speed set within 400 rpm or more and 3600 rpm or less allows for the preferable performance as optical equipment.

DESCRIPTION OF REFERENCE SIGNS

10 Rotation driving source
11 Rotor

12 Electromagnetic coil
13 Front housing
23 Tubular rotation shaft
33 First single-mode optical fiber
34 Second single-mode optical fiber
35 Optical path correcting means
35a First optical path correcting means
35b Second optical path correcting means
35c Optical path correcting means
41, 42 Bearing member
51 Light converging means
63 Optical path conversion element

The invention claimed is:

1. An optical imaging probe for guiding rearward a light entering a front end, comprising:
a rotation driving source having a rotor arranged in a substantially cylindrical shape and a substantially cylindrical coil having an inner circumference configured to cover a peripheral of the rotor, the rotation driving source being adapted to drive and rotate the rotor;
a first single-mode optical fiber inserted and fixed over an axial direction in a rotation center side of the rotor, a front end of which a light is able to enter;
a second single-mode optical fiber supported at a rear end side of the first single-mode optical fiber in a non-rotatable manner; and
a gap and optical path correcting means interposed between the first single-mode optical fiber and the second single-mode optical fiber,
wherein the optical path correcting means is adapted to expand and collimate a light transmitted from one of the first and second single-mode optical fibers and pass the light through the gap, and then guide the light to the other one of the first and second single-mode optical fibers,
wherein the optical imaging probe further includes a tubular rotation shaft fixed in an axial direction in a rotation center side of the rotor and supported in a rotatable manner,
wherein an end face of the first single-mode optical fiber is inserted within the tubular rotation shaft with an end of the first single-mode optical fiber forming a substantially flat plane with an end of the tubular rotation shaft.

2. The optical imaging probe according to claim 1, wherein the optical path correcting means includes first optical path correcting means connected to the first single-mode optical fiber and second optical path correcting means connected to the second single-mode optical fiber, and has the gap between the two optical path correcting means.

3. The optical imaging probe according to claim 2, wherein the tubular rotation shaft is supported in a rotatable manner in a state where an end of the tubular rotation shaft protrudes from the rotor in the axial direction, wherein a connection portion of the first single-mode optical fiber and the first optical path correcting means is disposed inside the tubular rotation shaft.

4. The optical imaging probe according to claim 3 further comprising a bearing member for supporting the tubular rotation shaft in a rotatable manner, wherein the bearing member includes a dynamic pressure bearing adapted to generate a high lubricating oil film pressure locally at multiple positions in a circumference direction.

5. The optical imaging probe according to claim 3 further comprising a bearing member for supporting the tubular rotation shaft in a rotatable manner, wherein the bearing member includes a dynamic pressure bearing adapted to generate a high lubricating oil film pressure locally at multiple positions in a circumference direction; and
wherein an optical path conversion element adapted to convert a direction of a light guided by the first single-mode optical fiber into an intersecting direction with respect to an axial direction of the tubular rotation shaft is provided in a front side of the first single-mode optical fiber.

6. The optical imaging probe according to claim 3 further comprising a bearing member for supporting the tubular rotation shaft in a rotatable manner, wherein the bearing member includes a dynamic pressure bearing adapted to generate a high lubricating oil film pressure locally at multiple positions in a circumference direction; and
wherein the rotor is rotated continuously at a number of revolution of 400 rpm or more and 3600 rpm or less.

7. The optical imaging probe according to claim 1, wherein an optical path conversion element adapted to convert a direction of a light guided by the first single-mode optical fiber into an intersecting direction with respect to an axial direction of the tubular rotation shaft is provided in a front side of the first single-mode optical fiber.

8. The optical imaging probe according to claim 7, wherein the rotor is rotated continuously at a number of revolution of 400 rpm or more and 3600 rpm or less.

9. The optical imaging probe according to claim 1, wherein the rotor is rotated continuously at a number of revolution of 400 rpm or more and 3600 rpm or less.

10. The optical imaging probe according to claim 1, wherein the optical path correcting means includes first optical path correcting means connected to the first single-mode optical fiber and second optical path correcting means connected to the second single-mode optical fiber, and has the gap between the two optical path correcting means; and
wherein an optical path conversion element adapted to convert a direction of a light guided by the first single-mode optical fiber into an intersecting direction with respect to an axial direction of the tubular rotation shaft is provided in a front side of the first single-mode optical fiber.

11. The optical imaging probe according to claim 1, wherein the optical path correcting means includes first optical path correcting means connected to the first single-mode optical fiber and second optical path correcting means connected to the second single-mode optical fiber, and has the gap between the two optical path correcting means; and
wherein the rotor is rotated continuously at a number of revolution of 400 rpm or more and 3600 rpm or less.

12. The optical imaging probe according to claim 1, wherein the optical path correcting means is a graded index optical fiber.

13. The optical imaging probe according to claim 1, further comprising a bearing member for supporting the tubular rotation shaft in a rotatable manner,
wherein the bearing member is formed in a substantially cylindrical shape and has an inner circumference on which a plurality of grooves extending in the axial direction are formed and arranged by predetermined pitches in a circumferential direction.

14. An optical imaging probe for guiding rearward a light entering a front end, comprising:
a rotation driving source having a rotor arranged in a substantially cylindrical shape and a substantially cylindrical coil having an inner circumference configured to cover a peripheral of the rotor, the rotation driving source being adapted to drive and rotate the rotor;

a first single-mode optical fiber inserted and fixed over an axial direction in a rotation center side of the rotor, a front end of which a light is able to enter;

a second single-mode optical fiber supported at a rear end side of the first single-mode optical fiber in a non-rotatable manner; and a gap and optical path correcting means interposed between the first single-mode optical fiber and the second single-mode optical fiber, wherein the optical path correcting means is adapted to expand and collimate a light transmitted from one of the first and second single-mode optical fibers and pass the light through the gap, and then guide the light to the other one of the first and second single-mode optical fibers, wherein the optical imaging probe further includes a tubular rotation shaft fixed in an axial direction in a rotation center side of the rotor and supported in a rotatable manner, wherein the first single-mode optical fiber contacts, by an outer surface of the first single-mode optical fiber, with an inner surface of the tubular rotation shaft over a substantially whole length of the first single-mode optical fiber in the axial direction and a substantially whole circumference, and integrally rotates with the tubular rotation shaft.

* * * * *